United States Patent [19]
Yen et al.

[11] Patent Number: 5,861,391
[45] Date of Patent: Jan. 19, 1999

[54] USE OF DEHYDROEPIANDROSTERONE TO TREAT PRIMARY ADRENAL INSUFFICIENCY AND ADDISON'S DISEASE

[75] Inventors: Samuel S.C. Yen, La Jolla; Brian Berger, San Diego, both of Calif.

[73] Assignee: Research Development Foundation, Carson City, Nev.

[21] Appl. No.: 790,921

[22] Filed: Jan. 29, 1997

[51] Int. Cl.⁶ ...................................................... A61K 31/56
[52] U.S. Cl. ............................................ 514/170; 514/178
[58] Field of Search ...................................... 514/170, 178

[56] References Cited

PUBLICATIONS

Filipponi et al, Archivio per le Scienze Mediche 136(1), 17–24 1979.
Embase Accession No. 94125338, Fujii et al, 1994.
CA 116:51817, Vermeulen et al, 1991.
CA 91: 190917, Filipponi et al, 1979.
Merck Manual, pp. 1050–1054, 1987.

*Primary Examiner*—Rebecca Cook
*Attorney, Agent, or Firm*—Benjamin Aaron Adler

[57] ABSTRACT

The present invention provides a method of treating an individual with primary adrenal insufficiency, comprising the step of administering an effective amount of dehydroepiandrosterone to said individual. Also provided is a method of treating an individual with adrenal failure secondary to dysfunctions of the hypothalamus and/or pituitary gland, comprising the step of administering an effective amount of dehydroepiandrosterone to said individual and a method of treating an individual with adrenal insufficiency due to acquired human immunodeficiency syndrome (AIDS), comprising the step of administering an effective amount of deyhydroepiandrosterone to said individual.

15 Claims, 4 Drawing Sheets

USE OF DEHYDROEPIANDROSTERONE TO TREAT PRIMARY ADRENAL INSUFFICIENCY AND ADDISON'S DISEASE

BACKGROUND OF THE INVENTION

1. Field of the Invention

The present invention relates generally to the fields of endocrinology and pharmacology. More specifically, the present invention relates to the use of dehydroepiandrosterone to treat primary adrenal insufficiency and Addison's disease.

2. Description of the Related Art

In 1855, Thomas Addison described the clinical features, natural history and autopsy findings of the disease that now bears his name. Addison's disease is a rare condition of primary adrenal insufficiency resulting from destruction of the adrenal gland and is caused by a variety of disorders, the most common of which is "autoimmune in origin", Oelkers, W. *Adrenal Insufficiency. N Eng J Med* 1996 335:1206–1212. The incidence of the disease is 40–60 cases per million young adults with a female/male ratio of 10 to 1 Mason, A. S., et al. *Epidemiological and Clinical Picture of Addison's Disease. Lancet* 1968, 2:744–747. In this condition, all three zones of the adrenal cortex are affected by the destructive processes (3,4). Consequently inadequate adrenal secretion of glucocorticoid, mineralocorticoid and androgen precursors such as dehydroepiandrosterone (DHEA) and dehydroepiandrosterone-sulfate (DS) occurs, Yamaji, T. et al. *Plasma DHEAS In Normal And Pathological Conditions. J. Clin Endocrinol Metab* 1969, 29: 273 and Urban, M. et al., *Androgens In Pubertal Males With Addison's Disease. J Clin Endocrinal Metab* 1980 51:925–929.

The onset of manifestation is usually gradual, going first through a stage of partial adrenal deficiency and followed sometime later by the overt cortisol deficiency which results clinically in nausea and vomiting, weight loss and anorexia. It is also associated with fever and hypoglycemia. In cases where mineralocorticoid production is decreased, hyponatremia and hyperkalemia occur. Hyperpigmentation of mucosa and skin occurs due to excessive pituitary ACTH secretion (secondary to the lack of cortisol feedback) and the associated overproduction of MSH-like peptides with pigmenting effect of the skin and mucus membranes, Mains, R. E., et al., *Synthesis And Secretion Of Corticotrophins, Melantrophins And Endorphins By Rat Immediate Pituitary Cells. J Biol Chem* 1979, 254:7885–7894 and Carter, R. J., et al., *Melanotrophin Potentiating Factor Is The C-Terminal Tetrapeptide Of Human β-Lipotrophin. Nature* 1979, 279:34–75. Not infrequently the autoimmune processes also involve other endocrine glands and hypothyroidism and premature ovarian failure may be part of the clinical manifestation, Oelkers, W. *Adrenal Insufficiency. N Eng J Med* 1996, 335:1206–1212, Irvine, W. J., et al. *Adrenocortical Insufficiency. Clin Endocrinol Metab Metab* 1972, 1:549–594, Mason, A. S., et al. *Epidemiological And Clinical Picture Of Addison's Disease.* Lancet 1968, 2:744–747, Eisenbarth, G. S., et al. *The Immunoendocrinopathy Syndromes.* In: Wilson, J. D., Foster, D. W., Ed. *Williams Textbook Of Endocrinology,* Saunders, Philadelphia, 1992: 1555–1566, Nerup, J. *Addison's Disease.* Clinical Studies. A report of 108 cases. *Acta Endocrinol* 1974, 76: 27–141, Spinner, M. W., et al. *Clinical And Genetic Heterogeneity In Idiopathic Addison's Disease And Autoimmune Hypoparathyroidism. J Clin Endocrinal Metab* 1968, 28: 795–804.

While replacements of glucocorticoids and mineralocorticoids are standard management of Addison's disease, no attempts to replace adrenal androgen have been properly made to date. Oelkers, W., *Adrenal Insufficiency, N Eng J Med,* 1996, 335:1206–1212. Patients with Addison's disease frequently complain of fatigue, loss of pubic and axillary hair, decreased libido and muscle weakness in spite of adequate replacement of adrenal corticoids. Burke, C. W. *Primary Adrenocortical Failure.* In: Grossman A. *Clinical Endocrinology,* Ed. Oxford: Blackwell: 1992:393–404, Zelissen P. M., et al. *Effect Of Glucocorticoid Replacement Therapy On Bone Mineral Density In Patients With Addison's Disease. Ann Int Med,* 1994, 120:207–210 and Riedel, M., et al. *Quality Of Life In Patients With Addison's Disease: Effects Of Different Cortisol Replacement Modes. Exper Clin Endocrinol,* 1993, 101:106–111.

The prior art is deficient in the lack of effective means of treating Addison's disease and primary or secondary adrenal insufficiency. The present invention fulfills this longstanding need and desire in the art.

SUMMARY OF THE INVENTION

The present invention shows that administration of dehydroepiandrosterone to individuals with primary adrenal insufficiency improves or reversed their debilitating symptoms which include chronic fatigue, decreased muscle strength, increased body fat mass, decreased bone mineral density, insomnia, depression and decreased libido in both male and female patients. The invention provides for the use of dehydroepiandrosterone and pharmaceutical compositions thereof, with conventional replacement of glucocorticoids and mineralcorticoids as a specific therapy to improve the disabling symptoms of Addison's disease and primary adrenal insufficiency. Furthermore, the present invention provides for the use of dehydroepiandrosterone and pharmaceutical compositions thereof, with conventional replacement of glucocorticoids and mineralcorticoids as a specific therapy to improve the disabling symptoms in patients with adrenal failure secondary to dysfunctions of the hypothalamus and/or pituitary gland. The present invention provides for the use of dehydroepiandrosterone and pharmaceutical compositions thereof, with conventional replacement of glucocorticoids andmineralcorticoids as a specific therapy to improve the disabling symptoms in patients with adrenal insufficiency due to acquired human immunodeficiency syndrome (AIDS), Oelkers, W. *Adrenal Insufficiency. N Eng J Med* 1996, 335:1206–1212, Sellmeyer, D. E., et al. *Endocrine And Metabolic Disturbances In Human Immunodeficiency Virus Infection And The Acquired Immune Deficiency Syndrome. Endo Rev* 1996, 17(5): 518–532 and Piérola G., et al. *Clinical Features Of Adrenal Insufficiency In Patients With Acquired Immunodeficiency Syndrome. Clin Endocrinal* 1996, 45: 97–101.

In one embodiment of the present invention, there is provided a method of treating an individual with primary adrenal insufficiency, comprising the step of administering an effective amount of dehydroepiandrosterone to said individual.

In another embodiment of the present invention, there is provided amethod of treating an individual with adrenal failure secondary to dysfunctions of the hypothalamus and/ or pituitary gland, comprising the step of administering an effective amount of dehydroepiandrosterone to said individual.

In yet another embodiment of the present invention, there is provided a method of treating an individual with adrenal insufficiency due to acquired human immunodeficiency syndrome (AIDS), comprising the step of administering an effective amount of dehydroepiandrosterone to said individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
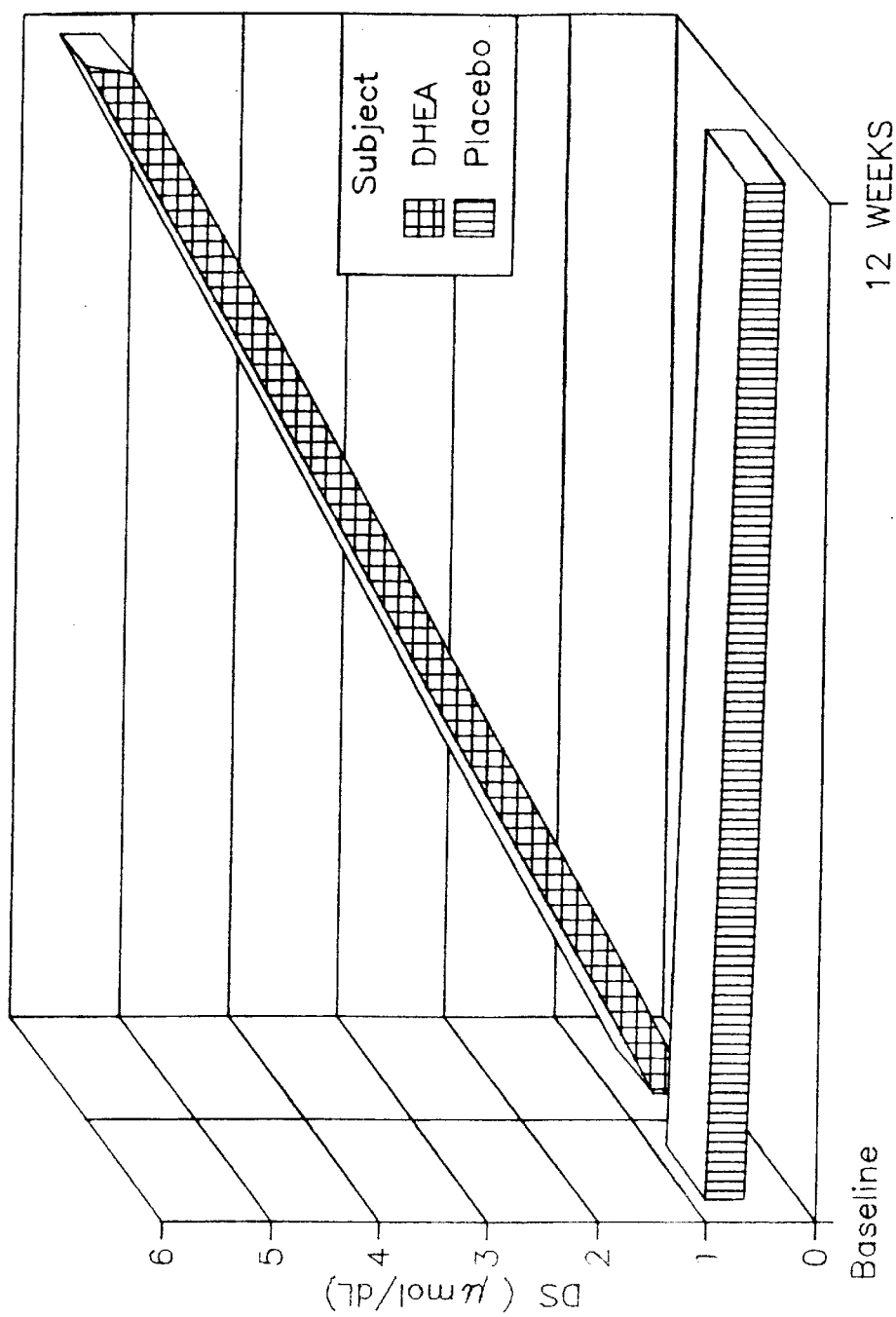
FIG. 1 shows the change in serum DS levels after 12 weeks of oral administration of DHEA (50 mg) nightly or placebo in two patients with Addison's disease.

The present invention is directed to a method of treating an individual with primary adrenal insufficiency, comprising the step of administering an effective amount of dehydroepiandrosterone to said individual. Preferably, the dehydroepiandrosterone is administered in a dose of from about 0.25 mg/kg to about 2.0 mg/kg. Most preferably, the dehydroepiandrosterone is administered in a daily dose of 50 mg. In this embodiment of the present invention, the method may further comprise administering a corticosteroid before or after the dehydroepiandrosterone. Preferably, the corticosteroid is either a glucocorticoid and/or a mineralcorticoid.

The present invention is also directed to a method of treating an individual with adrenal failure secondary to dysfunctions of the hypothalamus and/or pituitary gland, comprising the step of administering an effective amount of dehydroepiandrosterone to said individual. Preferably, the dehydroepiandrosterone is administered in a dose of from about 0.25 mg/kg to about 2.0 mg/kg. Most preferably, the dehydroepiandrosterone is administered in a daily dose of 50 mg. In this embodiment of the present inention, the method may further comprise administering a corticosteroid before or after the dehydroepiandrosterone. Preferably, the corticosteroid is either a glucocorticoid and/or a mineralcorticoid.

The present invention is also directed to a method of treating an individual with adrenal insufficiency due to acquired human immunodeficiency syndrome (AIDS), comprising the step of administering an effective amount of dehydroepiandrosterone to said individual. Preferably, the dehydroepiandrosterone is administered in a dose of from about 0.25 mg/kg to about 2.0 mg/kg. Most preferably, the dehydroepiandrosterone is administered in a daily dose of 50 mg. In this embodiment of the present inention, the method may further comprise administering a corticosteroid before or after the dehydroepiandrosterone. Preferably, the corticosteroid is either a glucocorticoid and/or a mineralcorticoid.

It is specifically contemplated that pharmaceutical compositions may be prepared using for the methods of the present invention using dehydroepiandrosterone. In such a case, the pharmaceutical composition comprises dehydroepiandrosterone and a pharmaceutically acceptable carrier. A person having ordinary skill in this art would readily be able to determine, without undue experimentation, the appropriate dosages and routes of administration of the novel steroid of the present invention.

The present invention shows that the adrenal sex steroid dehydroepiandrosterone, when administered by oral or sublingual routes in the form of a gelatin capsule restores the dehydroepiandrosterone-S levels in patients with Addison's disease and improves their disabling symptoms such as fatigue, decreased libido, decreased bone mineral density, muscle weakness and decreased physical and psychological well being.

Dehydroepiandrosterone may be formulated as a powder and then placed into gelatin capsules with each capsule containing 50 mg. Other suitable dosage forms for oral administration include pills, tablets (coated or otherwise), elixirs, suspensions, syrups or inhalations and controlled release forms thereof.

Dehydroepiandrosterone may also be administered in the form of an implant or formulated transdermal application, e.g., in the form of a transdermal patch and cream or in sublingual form. Dehydroepiandrosterone and the corticosteroid agent may be combined in a single dosage form or in discreet dosage forms. Dehydroepiandrosterone and the mineralcorticoid may be combined in a single dosage form or in discreet dosage forms.

The present invention is thus directed to a pharmaceutical composition, comprising dehydroepiandrosterone and a pharmaceutically acceptable carrier or diluent. In order to a use a dehydroepiandrosterone or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of dehydroepiandrosterone and a pharmaceutically acceptable carrier or diluent.

Dehydroepiandrosterone, pharmaceutically acceptable salt thereof and pharmaceutical compositions incorporating such, may be conveniently administered by any of the routes conventionally used for drug administration, e.g., orally, topically, parenterally, or by inhalation. Dehydroepiandrosterone may be administered in conventional dosage forms prepared by combining dehydroepiandrosterone with standard pharmaceutical carriers according to conventional procedures. Dehydroepiandrosterone may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of adminstration and other well known variable. The carrier(s) must be "acceptable" in the sense of being compatible with the other ingredients of the formulation and not deleterious to the recipient thereof.

The pharmaceutical carrier employed may be, for example, either a solid or a liquid. Representative solid carriers are lactose, terra alba, sucrose, talc, gelatin, agar, pectin, acacia, magnesium sterate, stearic acid and the like. Representative liquid carriers include syrup, peanut oil, olive oil, water and the like. Similarly, the carrier may include time delay material well known in the art such as glyceryl monosterate or glyceryl disterarate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension.

For all methods of use of the present invention disclosed herein for dehydroepiandrosterone, the daily oral dosage regiment will preferably be from about 0.1 to about 3.0 mg/kg of total body weight, preferably from about 0.25 to 2.0 mg/kg and more preferably from about 0.5 to 1 mg/kg. The daily parenteral dosage regiment will preferably be from about 0.1 to about 10 mg/kg of total body weight, preferably from about 0.2 to 2 mg/kg. It will also be recognized by one of skill in this art that the optimal quantity and spacing of individual dosages of a compound of the present invention, or a pharmaceutically acceptable salt thereof, will be determined by the nature and extent of the condition being treated and that such optimums can be determined by conventional techniques.

Suitable pharmaceutically acceptable salts are well known to those skilled in the art and include basic salts of inorganic and organic acids, such as hydrochloric acid, hydrobromic acid, sulphuric acid, phophoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of dehydroepiandrosterone may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

The following examples are given for the purpose of illustrating various embodiments of the invention and are not meant to limit the present invention in any fashion.

EXAMPLE 1

Study

In a prototype study with patients with Addison's disease, dramatic differences were observed in clinical improvement of certain symptom scores between the patient taking dehydroepiandrosterone versus (50 mg/day) the patient taking placebo after 12 weeks of treatment. Subject 1 was a 55 year old Caucasian female with a history of Addison's disease for 26 years. She had been on a steady dose of hydrocortisone (30 mg/day) and Florinef (0.1 mg/day) for over 10 years. The patient also had a history of hypothyroidism and was euthyroid on levothyroxin (0.1 mg/day). Baseline interview revealed that the patient had multiple complaints including physical fatigue, dry skin, weakness, depression and poor sleep.

Figure 2:
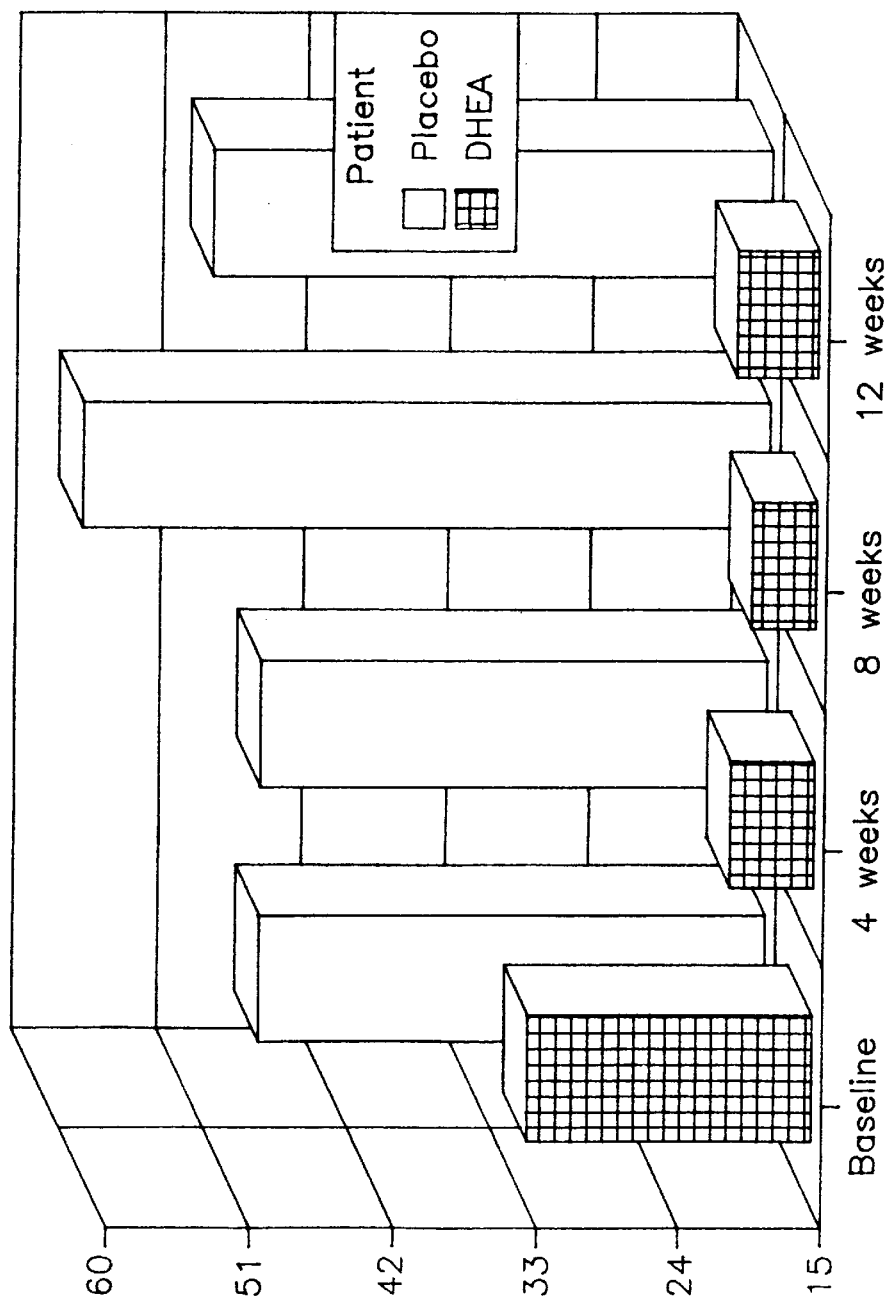
FIG. 2 shows the difference in self-assessment of fatigue in subjects on DHEA (50 mg/day) versus subjects on placebo over a period of 12 weeks.
Figure 3:
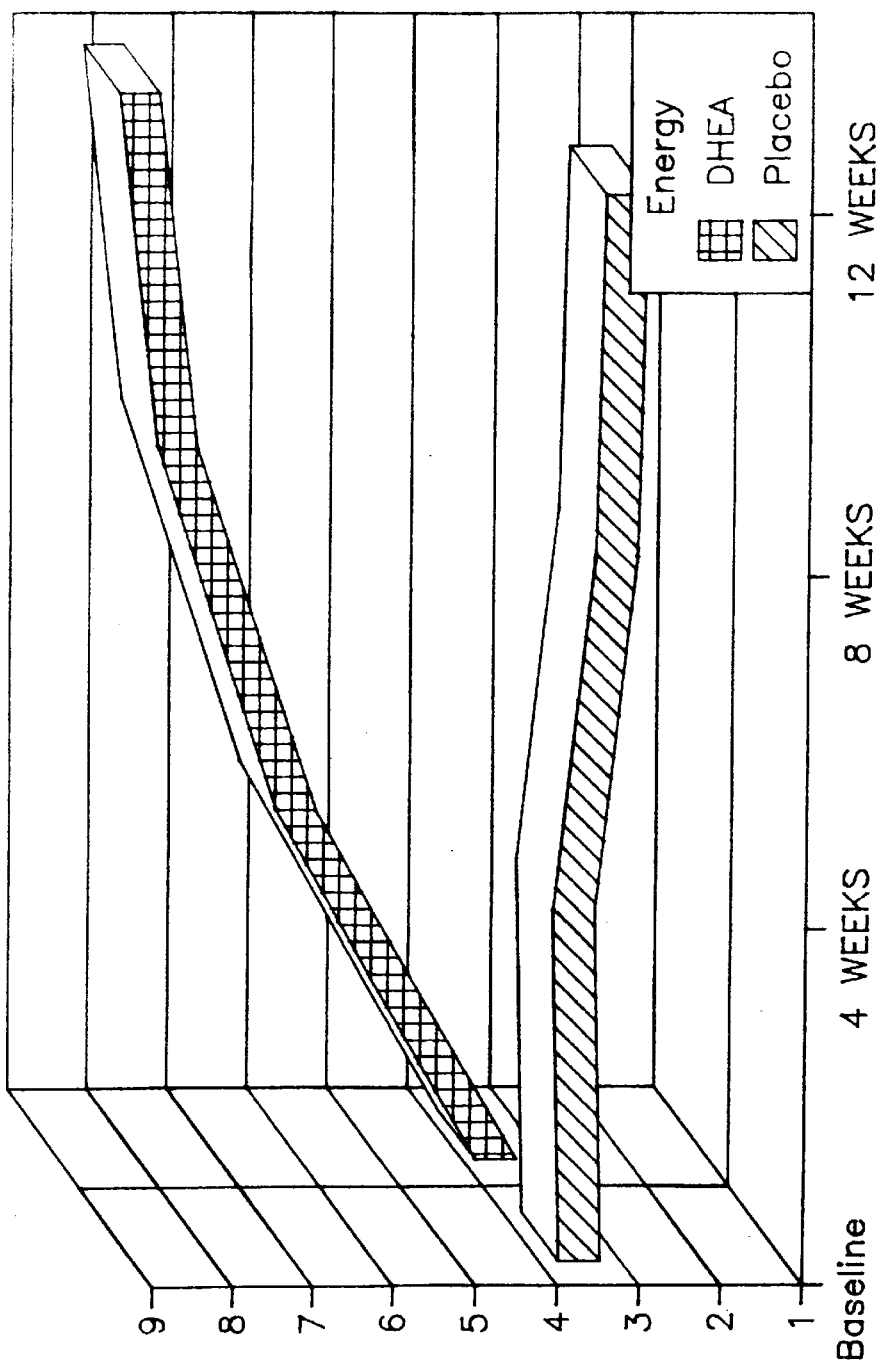
FIG. 3 shows the energy as measured by visual analogue scale for a subject on DHEA (50 mg/day) versus the subject on placebo for 12 weeks.
Figure 4:
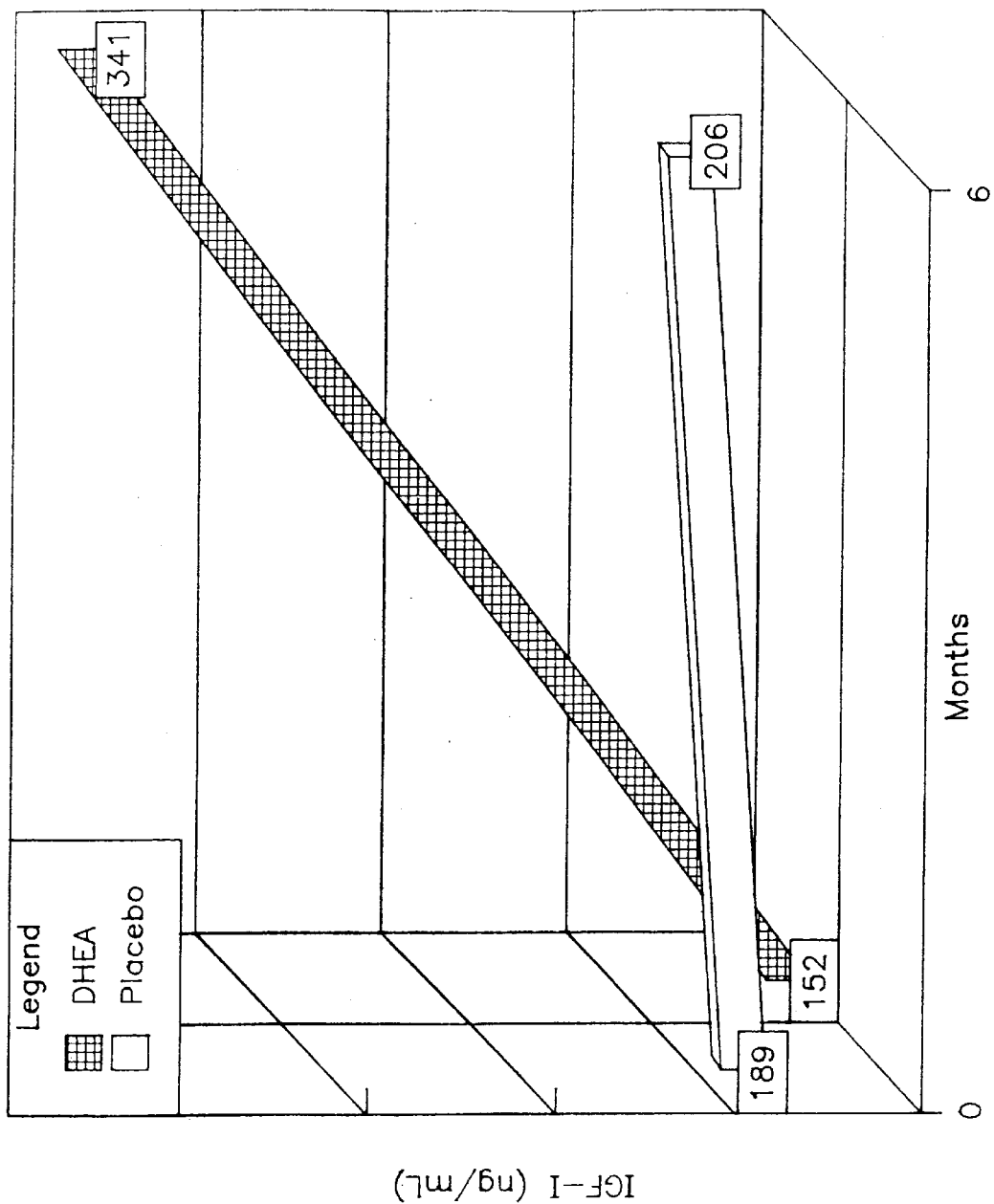
FIG. 4 shows an increase in insulin-like growth Factor-I (IGF-I) levels in a subject with Addison's disease on DHEA (50 mg/day) vs. the subject on placebo over a six-month period (normal value 250≠20 mg/ml).

At baseline measurement, the patient had a very low dehydroepiandrosterone-S level of less than 0.42 $\mu$g/ml. The range for a normal young female is 0.51–3.39 $\mu$g/ml. After twelve weeks on dehydroepiandrosterone at a dose of 50 mg/day, the patient achieved a "young female" physiologic dehydroepiandrosterone-S level of 5.67 $\mu$g/ml (FIG. 1). In addition, fatigue was markedly improved as reflected by the self-assessment scale (FIG. 2) and increased energy was seen in the visual analogous scale (FIG. 3). In addition, insulin-like growth factor (IGF-I) levels doubled after 6 months of treatment (FIG. 4).

EXAMPLE 2

Subject 2 was a 72 year old Caucasian male with a history of Addison's disease for 32 years. The patient had been on a steady dose of hydrocortisone (35 mg/day) and Florinef (0.1 mg/day) for over 5 years. The patient also had a history of hypothyroidism and was euthyroid on levothyroxin (0.15 mg/day).

The baseline interview showed that the patient had multiple complaints including physical fatigue, decreased energy, weight gain, weakness, depression, poor appetite, and poor sleep. At baseline measurement, the patient had a very low dehydroepiandrosterone-S level of less than 0.42 $\mu$g/ml. The normal young male range is 1.5–4.7 $\mu$/ml. After 12 weeks on placebo, the patient's dehydroepiandrosterone-S levels remained at 0.42 $\mu$/ml. There was no change in fatigue based on the self-assessment scale (FIG. 2) and the patient continued to have low energy as seen in the visual analogue scale (FIG. 3). In addition, there was no significant change in IGF-I levels (FIG. 4).

EXAMPLE 3

Study Design

The design of the 12-month experiment is a 6-month stratified random assigned double-blind parallel study with one arm receiving 6 months of dehydroepiandrosterone 50 mg/day (IND#32,554) and the other receiving placebo for the same duration. Stratification into two groups is performed prior to randomization: (1) above age 45; and (2) below age 45. Following this, all of the patients are invited to participate in an open trial of dehydroepiandrosterone for an additional 6 months.

EXAMPLE 4

Objective parameters

All blood tests including safety labs, muscle strength tests (grip strength), 24-hour assessments of the somatotrophic axis, basal metabolic rate, insulin/glucose levels, grip strength, and bone mineral density (BMD) and body composition as measured by dual x-ray absorptiometry (DEXA) are made at baseline and 6 months of treatment. BMD and body composition are measured at 12 months as well. In addition, in those patients that continue with the 6month open trial, safety and endocrine parameters are measured at both 9 months and 12 months. In addition, safety labs and endocrine parameters (not including GH) are measured between the $12^{th}$ and $14^{th}$ week of the study. Those patients electing to continue with the 6-month open trial have the safety and endocrine parameters measured at 9 months and 12 months.

Quality of life, sleep, and libido questionnaires are evaluated at weekly intervals throughout the study. These questionnaires are mailed monthly to the patients and completed at home. These issues are evaluated weekly in the open trial. Post-study evaluation are carried out promptly after all data has been completed to determine hormonal, quality of life and body composition changes. Three months after completion of the study, the effectiveness of dehydroepiandrosterone replacement is determined.

EXAMPLE 5

Procedures

All studies are conducted at the Clinical Research Center (CRC). A single outpatient visit is employed at Perlman Ambulatory Care Center before initiating the study at the patient's expense, both for assessments of efficacy and for monitoring potential safety/adverse effects. Medications are distributed at baseline and then at 3, 6, and 9 months. Patients are admitted to the CRC on two separate occasions for 24 hours for two of the objective evaluations. Patients also have one blood sample drawn at 12–14 weeks, and at 36–38 weeks as outpatients. Safety parameters (see below) are measured at all inpatient and outpatient visits.

EXAMPLE 6

Objective data analysis at baseline and 6 month intervals

For determination of GH, GHBP, IGF-I, IGFBP-1, IGFBP-3 (anabolic) levels, blood is drawn every 10 minutes for 24 hours from an intravenous catheter to assay for GH. Fasting blood drawn between 08:00–09:00 is used to assay for GHBP, IGF-I, IGFBP-1 and IGFBP-3. An immunofunctional assay for GHBP and immunofluorescent radiometric assay for IGFBP-1 have been established. IGF-1 and IGFBP-3 measurements are done by RIA kits from Corning-Nichols Laboratory.

EXAMPLE 7

Urine measurements 24 hours collection after discarding the first void given between 07:00 and 9:00am, measurements are performed for assessment of total volume, urinary creatinine, 17-ketosteroids and free cortisol.

EXAMPLE 8

Muscle strength

Palmar strength is assessed using a dynamometer. Subjects are seated with their shoulder adducted and neutrally rotated, elbow flexed at 90 with the forearm in neutral position, and the wrist between 0 and 30 dorsiflexion and 0 and 15 ulnar deviation. For each strength test, the scores of three successive efforts are recorded for each hand and averaged (24,25,26).

EXAMPLE 9

Body composition (DEXA)

Using DEXA for body compositions reveal a significant ($p<0.001$) correlation coefficient of from 0.89–0.93 in predicting % body and regional fat (22). Both regional (arms, legs, trunk and head) and total body % fat and lean tissue mass (LTM) can be measured with a precision error of <1.5% and 1.5%, respectively (23,24). Total body scans with DEXA take only 10–20 minutes. Radiation dose is low 0.02 to 0.05 mrem. This is also performed with each inpatient visit and at twelve months.

EXAMPLE 10

Insulin secretion and Basal metabolic rate

Insulin and glucose levels is drawn at baseline, each hour, and every half hour after meals. Indirect calorimetry is the method by which the type of substrate utilization, and energy metabolism are estimated in vivo starting from gas exchange measurements. This is measured after patients rest for 60 minutes in semi-recumbent position. Three measurements are made during a 90 minute period each taking 12 minutes. The three values are averaged and oxygen consumption is converted to kilocalories.

EXAMPLE 11

Objective data analysis at 0, 3, 6, 9 and 12 months:

For lipids, the concentration of cholesterol, HDL, LDL, apolipoproteins A1 and B, free fatty acids (FFA), and LP(a) are measured by clinical chemistry from fasting blood. For hormonal parameters, the serum concentrations of androgens (DHT, T, A, dehydroepiandrosterone, dehydroepiandrosterone-S); estrogens (estrone, estradiol) SHBG; glycoproteins (LH, FSH), and plasma ACTH are measured by previously described RIA's from fasting plasma. For measurement of the IGF-I system, fasting blood drawn between 08:00–09:00 is used to assay for GHBP, IGF-I, IGFBP-1 and IGFBP-3.

EXAMPLE 12

Weekly subjective analysis

For measurement of well-being, four broad domains contribute to the overall quality of life effect: physical and occupational function; psychological state; social interaction; and somatic sensation (12). There are two broad areas of Quality of Life (QOL) assessed. The first measures psychological aspects of well being while the second measures the impact of intervention (the trial) on quality of life (QOL). There is no gold standard for quality of life measurements, Slevin, M. R., et al. *Who Should Measure Quality Of Life, The Doctor Or The Patient? Br J Cancer* 1988, 57:109–112 and Kaplan, R. M., et al. *Health-Related Quality Of Life Measurement For Evaluation Research And Policy Analysis. Health Pschol* 1982, 1:61–80. In a recent critique of QOL instruments, it was concluded that QOL can be suitably measured only by determining the opinions of subjects or patients and by supplementing or replacing the instruments developed by "experts" (13). For overall well being, a well-known test and validated indexes—General Well-Being Scale (14) is used. This self-administered questionnaire has a reliability coefficient of 0.745 and has been tested in the national health and nutrition examination survey (ages 25–74) (n=3380) for reliability and validity. This instrument is supplemented by open-ended questions as to the physical and psychological changes during the trial.

The Pittsburgh Sleep Quality Index is used to quantitatively measure sleep satisfaction (15). This is a self-rated questionnaire which assesses sleep quality and disturbances over the previous 1 month time interval. The reliability and validity of this questionnaire in healthy controls (age 24–83) has been shown and this tool has been used in several trials (16). Both a global score and seven component scores is obtained.

Libido in this trial means desire of sexual activity and frequency of intercourse. Due to the lack of any standard instruments for evaluating sexual function with drugs, the Crenshaw-Goldberg Sexual Desire Inventory (CGSDI) scales (17) is used. In addition, a visual analog scale for libido is administered to each patient on monthly intervals. A visual analog scale is used to assess libido (18).

A log book entailing the patient's daily medications and dosages is maintained by all of the patients throughout the 6 month study period. This is also part of the subjective assessment of the patient's well-being.

EXAMPLE 13

Safety parameters performed at baseline 3 and 6, 9 and 12 months

The following are measured: chemistry/Hematology-Chemistry: albumin; albumin/globulin ratio, alkaline phosphates, bilirubin (total and direct), bicarbonate, BUN/creatinine ratio, calcium, chloride, creatinine, globulin, aspartate aminotransferase and alanine aminotransferase.

Inorganic phosphorus, potassium, sodium, total protein, urea nitrogen and uric acid, thyroid stimulating hormone, free thyroxine, Glucose, plasma levels of Na, K, Phos, Ca, Mg, U, Cr. Urine analysis: specific gravity, appearance, acetone, protein, glucose, pH, bile, urobilinogen, occult blood, microscopic evaluation of sediment. Hematology: Red blood cell count, hemoglobin, hematocrit, white blood cell count and differential, platelet estimate, red blood cell indices.

EXAMPLE 14

Data Analysis

No interim analysis is done in this trial. Since dehydroepiandrosterone deficiency is not defined as a disease state, there are no ethical issues of non-treatment. Interim analyses do not refer to safety parameters that will be reviewed as they become available. Descriptive statistics such as distribution testing, means, variances and standard deviations are calculated for parameters. Standard errors are also calculated for means. To help with interpretation of data the overall data is graphed as well as individual data.

All the data generated is analyzed by interval data. Although significance testing is the main statistical tool, a strategy is developed for handling the complex trial data. Confidence intervals are also used for estimation as this provides a helpful indication of the uncertainty by presenting upper and lower bounds for the anticipated true treatment difference. Multiple repeated significance testing is not done as this increases the chance that a significant finding is found. To avoid this, a single primary end point is chosen.

Analysis of variance remains the most important statistical tool available for analysis of interval data. Assumptions which must be met are that the various comparison groups must be randomly constituted (allocation to groups is random and the sample from the population is random) and that the variance of the subgroups would be homogeneous. The design is set so as to satisfy both requirements. ANOVA is a robust technique. Repeated measures ANOVA are used in addressing some objectives. Three time points (baseline, 6 and 12 months) are used.

Correlation and regression techniques are used to establish relationships between variable and effects. Correlation techniques rely mainly on the Pearson produce moment correlation coefficient to measure degree of relatedness. If a strong correlation exists then linear regression can be used to help define the relationship between variables. In summary, the data is analyzed by two factor analysis of variance. The two main factors in the design are treatment and time with main outcome parameters being measures of the GH and IGF system.

EXAMPLE 15

Human subjects

The inclusion criteria are: (1) subjects must be over age 18; (2) subjects must be in good stable health as determined by medical history, clinical laboratory tests, mammogram within past year if over age 40 (if female), and physical exam; (3) subjects must have been on stable dose of glucocorticoids/mineralocorticoids over the past year; (4) subjects must have serum dehydroepiandrosterone levels <1.5 nmol/L; (5) female subjects may be on HRT (hormone replacement therapy) using any estrogen/progesterone combination in either cyclical or continuous regimen, and in either oral or transdermal administration method; (6) subjects must give voluntary, written consent and agree to observe all the study requirements.

EXAMPLE 16

Exclusion Criteria

The following characteristics are criteria for excluding a patient from the trial: history of estrogen/androgen dependent neoplasia; vascular disease, thrombotic disorders, or angina; active hepatic or gall bladder disease; if female, undiagnosed vaginal/uterine bleeding during the 6 months prior to the study initiation; if male, any history of androgen dependent neoplastic process excluding benign prostatic hyperplasia; clinically significant abnormalities in the medical history, physical exam, or mammography (if female); use of an investigational drug; endocrine disease, with the exception of controlled thyroid disease as evidenced by a normal TSH; any malignancy; elevated blood pressure (systolic >165mm Hg and/or diastolic >95mm Hg) on two readings taken at least 15 minutes apart in one visit; if female, no PAP smear within 1 year prior to initiating study, or PAP smear within year prior to initiating study showing any degree of dysplasia (LGSIL or higher).

Informed consent is obtained by one of the investigators both verbally and by means of an IRB approved consent form. Subjects will receive a copy of the consent form as well as a human subject bill of rights as required by our human subject committee. In addition, each subject will receive a wallet-size card containing all relevant phone numbers for appointments and for use in case of emergency.

Blood sampling: The amount of blood sampled in this trial is not more than 500 cc per 24 hour study. This may produce slight anemia. Hemoglobin is checked monthly on all subjects to ensure that there is no baseline anemia (hgb.<10.5 gm). Patients with hgb<10.5 gm are excluded from the 24 hours GH collection.

Procedures: The risk of DEXA includes possible subject discomfort. The total time needed to scan is about 20 minutes. The total radiation exposure is less than that of a chest x-ray. Although no known amount of radiation is considered safe, the risk of exposure to this amount of radiation is so small that it is difficult to measure. The risk of grip strength is minimal; possible mild hand stiffness. The risk of indirect calorimetry is a possible feeling of claustrophobia; the subjects are enclosed in a hood for one hour. The risk of administering questionnaires is thought to be negligible.

EXAMPLE 17

Medications

Dehydroepiandrosterone: The risk of nightly chronic administration of dehydroepiandrosterone in healthy adults are minimal to date; possible effects of increased anabolism. Serum chemistries are evaluated every 3 months as will hematologic parameters. Should any ill effects occur, participation is discontinued. Irregular vaginal bleeding: any female that complains of irregular vaginal bleeding will undergo endometrial biopsy to rule out neoplastic process.

Patients with adrenal insufficiency may receive medical benefit from a new treatment as well as the benefit of an increased level of medical care and monitoring. Other benefits include education about aging and importance about sex steroids. The records and data obtained from history and physical exam of the subjects are used for research purposes as well as providing pertinent information to their own physician when requested.

Administration of dehydroepiandrosterone may have potential benefits of increased anabolism in these patients. In view of potential health benefits and the lack of identified risks in 6 or 12 month exposure in humans at low doses, the risk/benefit ratio is heavily in favor of performing this study.

The following references were cited herein:

1. Burke CW. Primary adrenocortical failure. In: Grossman A. Clinical Endocrinology. Ed. Oxford: Blackwell; 1992:393–404.
2. Eisenbarth GS, Jackson RA. The immunoendocrinopathy syndromes. In: Wilson JD, Foster DW, Ed. Williams textbook of Endocrinology, Saunders, Philadelphia, 1992:1555–66.
3. Irvine WJ, Barnes EW. Adrenocortical insufficiency. *Clin Endocrinol Metab* 1972, 1:549–94.
4. Khalid BAK, Burke CW, Hurley DM, Funder JW, Stockigt JR. Steroid replacement in Addison's disease and in subjects adrenalectomized for Cushing's disease: comparison of various glucocorticoids. *J Clin Endocrinol Metab* 1982, 55:551–9.
5. Sizonenko PC, Paunier L. Correlation of plasma dehydroepiandrosterone, testosterone, FSH and LH with stages of puberty and in patients with Addison's disease and premature ovarian failure. *J Clin Endocrinol Metab* 1975, 41:894.
6. Korth-Schutz S, Levine L, New M, Chow D. Serum androgens in normal prepubertal and pubertal children and children with precocious adrenarche. *J Clin Endocrinol Metab* 1976, 42:117.
7. Hopper B, Yen SSC. Circulating concentrations of dehydroepiandrosterone and dehydroepiandrosterone-S during puberty. *J Clin Endocrinol Metab* 1975, 40:458.
8. Yamaji T, Ihayashi H. Plasma dehydroepiandrosterone-S in normal and pathological conditions. *J Clin Endocrinol Metab* 1969, 29:273.
9. Urban M, Lee P, Gutsi J, Migeon C. Androgen in pubertal males with Addison's' disease. *J Clin Endocrinol Metab* 1980, 51:925.
10. Krohn K, Uibo R, Aavik E, Peterson P, Savilahti K. Identification by molecular cloning of an autoantigen associated with Addison's disease as steroid 17 α-hydroxylase. *Lancet,* 1992, 339:770–3.
11. Morales AJ, Nolan JJ, Nelson JC, Yen SSC. Effects of replacement dose of dehydroepiandrosterone in men and women of advancing age. *J Clin Endocrinol Metab* 1994, 78:1360.
12. Slevin MR, Plant H, Lynch D, Drinkwater J, Gregory WM. Who should measure quality of life, the doctor or the patient? *Br J Cancer* 1988, 57:109–112.
13. Gill TM, Feinstein AR. A critical appraisal of the quality of quality-of-life measurements. *JAMA* 1994, 272:619.
14. Kaplan RM, Bush JW. Health-related quality of life measurement for evaluation research and policy analysis. *Health Psychol* 1982, 1:61–80.
15. Buysse DJ, Reynolds CF, Monk TH, Berman SR, Kopfer OJ. The Pittsburgh Sleep Quality Index: a new instrument for psychiatric practice and research. *Psych Res* 1989, 28:193–213.
16. Mendelson WB, Weingartner H, Greenblatt DG, Gillin JC. A clinical study of flurazepam. *Sleep* 1982, 5(4):350–360.
17. Crenshaw et al. Pharmacologic modification of psychosexual dysfunction. *J Sex Marital Therapy* 1987, 13(4):239–252.
18. Aitken RC. Measurement of feeling using visual analog scales. *Proc Roy Soc Med* 1969, 2:989–993.
19. Editorial. Quality of life and clinical trials. Lancet 1995;346:1–2.
20. Coons SJ, Kaplan RM. Assessing health-related quality of life; application to drug therapy. *Clin Therapeut* 1992;14(6):854–858.
21. Riedel M, Wiese A, Schurmeyer TH, Brabant G. Quality of life in patients with Addison's disease: effects of different cortisol replacement modes. *Exper Clin Endocrinol* 1993;101:106–111.
22. Dunn et al., *Soc Nuc Med Mtg,* Wash, D. D. Jun. 19–22, 1990.
23. Mazess RB, Barden HS, Bisek JP, Hanson J. 1990. Dual-energy x-ray absorptiometry for total-body and regional bone-mineral and soft tissue composition. *Am J Clin Nutr* 51:106–1112.
24. Florkowski CM, Holmes SJ, Elliot JR, Donald RA, Espiner EA. Bone mineral density is reduced in female but not male subjects with Addison's disease. *N Z Med J* 1994;107:52–53.
25. Mathiowetz V, Kashman N, Volland G, et al. Grip and pinch strength: normative data for adults. Arch Phys Rehabil 1985;66–72.
26. Mathiowetz V, Weber K, Volland G, Kashman. Reliability and validity of grip and pinch strength evaluations. J Hand Surg 1984;9:222–226.

Mason, A. S., et al. *Epidemiological and Clinical Picture of Addison's Disease. Lancet* 1968 2:744–747.
Sellmeyer, D. E., et al. *Endocrine And Metabolic Disturbances In Human Immunodeficiency Virus Infection And The Acquired Immune Deficiency Syndrome. Endo Rev* 1996, 17(5): 518–532.
Pierola G., et al. *Clinical Features Of Adrenal Insufficiency In Patients With Acquired Immunodeficiency Syndrome. Clin Endocrinal* 1996, 45: 97–101.
Burke, C. W. *Primary Adrenocortical Failure. In: Grossman A. Clinical Endocrinology. Ed. Oxford: Blackwell:* 1992:393–404.
Canalis, E. *Mechanisms Of Glucocorticoid Action In Bone: Implications To Glucocorticord-Induced Osteoporosis. J. Clin Endocrinol Metab* 1996, 81(10): 3441–3447.
Zelissen P. M., et al. *Effect Of Glucocorticoid Replacement Therapy On Bone Mineral Density In Patients With Addison's Disease. Ann Int Med* 1994, 120:207–210.
Morales, A., et al., *Effects Of Replacement Dose Of Dehydroepiandrosterone In Men And Women Of Advancing Age. J Clin Endocrinol Metab* 1994, 78:1360–1367.
Oelkers, W. *Adrenal Insufficiency. N Eng J Med* 1996, 335:1206–1212.
Yamaji, T. et al. *Plasma DHEAS In Normal And Pathological Conditions. J. Clin Endocrinol Metab* 1969, 29: 273.
Urban, M. et al. *Androgens In Pubertal Males With Addison's Disease. J Clin Endocrinal Metab* 1980, 51:925–929.
Mains, R. E., et al. *Synthesis And Secretion Of Corticotrophins, Melantrophins And Endorphins By Rat Immediate Pituitary Cells. J Biol Chem* 1979, 254:7885–7894.
Carter, R., et al., *Melanotrophin Potentiating Factor Is The C-Terminal Tetrapeptide Of Human β-Lipotrophin. Nature* 1979, 279:34–75.
Irvine, W. J., et al. *Adrenocortical Insufficiency. Clin Endocrinol Metab Metab* 1972, 1:549–594.
Mason, A. S., et al. *Epidemiological And Clinical Picture Of Addison's Disease. Lancet* 1968, 2:744–747.
Eisenbarth, G. S., et al. *The Immunoendocrinopathy Syndromes.* In: Wilson, J. D., Foster, D. W., Ed. *Williams Textbook Of Endocrinology,* Saunders, Philadelphia, 1992: 1555–1566.
Nerup, J. *Addison's Disease.* Clinical Studies. A report of 108 cases. *Acta Endocrinol* 1974, 76: 27–141.
Spinner, M. W., et al. *Clinical And Genetic Heterogeneity In Idiopathic Addison's Disease And Autoimmune Hypoparathyroidism. J Clin Endocrinal Metab* 1968, 28: 795–804.
Riedel, M., et al. *Quality Of Life In Patients With Addison's Disease: Effects Of Different Cortisol Replacement Modes. Exper Clin Endocrinol* 1993, 101:106–111.

Slevin, M. R., et al. *Who Should Measure Quality Of Life, The Doctor Or The Patient? Br J Cancer* 1988, 57:109–112.

Kaplan, R., *Health-Related Quality Of Life Measurement For Evaluation Research And Policy, Health Pschol* 1982, 1:61–80.

Hoenig H, Groff G, Pratt K, et al. A randomized controlled trial of home exercise on the rheumatoid hand. J Rheumatol 1993;20:785–789.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating an individual with primary adrenal insufficiency comprising the step of administering an effective amount of dehydroepiandrosterone to said individual.

2. The method of claim 1, wherein said dehydroepiandrosterone is administered in a dose of from about 0.25 mg/kg to about 2.0 mg/kg.

3. The method of claim 1, wherein said dehydroepiandrosterone is administered in a dose of 50 mg.

4. The method of claim 1, further comprising administering a corticosteroid before or after said dehydroepiandrosterone.

5. The method of claim 4, wherein said corticosteroid is selected from the group consisting of a glucocorticoid and a mineralocorticoid.

6. A method of treating an individual with adrenal failure secondary to dysfunction of the hypothalamus or pituitary gland, comprising the step of administering an effective amount of dehydroepiandrosterone to said individual.

7. The method of claim 6, wherein said dehydroepiandrosterone is administered in a dose of from about 0.25 mg/kg to about 2.0 mg/kg.

8. The method of claim 6, wherein said dehydroepiandrosterone is administered in a dose of 50 mg.

9. The method of claim 6, further comprising administering a corticosteroid before or after said dehydroepiandrosterone.

10. The method of claim 9, wherein said corticosteroid is selected from the group consisting of a glucocorticoid and a mineralocorticoid.

11. A method of treating an individual with adrenal insufficiency due to acquired human immunodeficiency syndrome (AIDS), comprising the step of administering an effective amount of dehydroepiandrosterone to said individual.

12. The method of claim 11, wherein said dehydroepiandrosterone is administered in a dose of from about 0.25 mg/kg to about 2.0 mg/kg.

13. The method of claim 11, wherein said dehydroepiandrosterone is administered in a dose of 50 mg.

14. The method of claim 11, further comprising administering a corticosteroid before or after said dehydroepiandrosterone.

15. The method of claim 14, wherein said corticosteroid is selected from the group consisting of glucocorticoid and a mineralocorticoid.

* * * * *

UNITED STATES PATENT AND TRADEMARK OFFICE
CERTIFICATE OF CORRECTION

PATENT NO. : 5,861,391
DATED : January 19, 1999
INVENTOR(S) : Samuel S.C. Yen, et. al.

It is certified that error appears in the above-identified patent and that said Letters Patent is hereby corrected as shown below:

In Column 2, line 29, "mineralcorticoids" should read --mineralocorticoids--.

In Column 2, line 34, "mineralcorticoids" should read --mineralocorticoids--.

In Column 2, line 40, "andmineralcorticoids" should read --and mineralocorticoids--.

In Column 3, line 8, "matter" should read --manner--.

In Column 3, line 45, "mineralcorticoids" should read --mineralocorticoids--.

In Column 3, line 54, "inention" should read --invention--.

In Column 3, line 57-58, "mineralcorticoids" should read --mineralocorticoids--.

In Column 3, line 67, "inention" should read --invention--.

UNITED STATES PATENT AND TRADEMARK OFFICE
CERTIFICATE OF CORRECTION

PATENT NO. : 5,861,391
DATED : January 19, 1999
INVENTOR(S) : Samuel S. C. Yen, et. al.

It is certified that error appears in the above-identified patent and that said Letters Patent is hereby corrected as shown below:

In Column 4, line 3, "mineralcorticoids" should read --mineralocorticoids--.

In Column 4, line 33, "discreet" should read --discrete--.

In Column 4, line 34, "mineralcorticoids" should read --mineralocorticoids--.

In Column 4, line 35, "discreet" should read --discrete--.

In Column 4, line 38, please delete the word "a" at the end of the line.

In Column 5, lines 19 and 22, "regiment" should read --regimen--.

In Column 5, line 34, "phophoric" should read --phosphoric--.

UNITED STATES PATENT AND TRADEMARK OFFICE
CERTIFICATE OF CORRECTION

PATENT NO. : 5,861,391
DATED : January 19, 1999
INVENTOR(S) : Samuel S.C. Yen, et. al.

It is certified that error appears in the above-identified patent and that said Letters Patent is hereby corrected as shown below:

In Column 6, line 51, "6month" should read --6-month--.

In Column 6, line 63, "evaluation" should read --evaluations--.

In Column 8, line 46, "is" should read --are--.

In Column 8, line 61, please insert a comma after the word "baseline".

In Column 10, line 46, "risk" should read --risks--.

In Column 13, line 29, please insert a comma after the word "insufficiency".

UNITED STATES PATENT AND TRADEMARK OFFICE
CERTIFICATE OF CORRECTION

PATENT NO. : 5,861,391
DATED : January 19, 1999
INVENTOR(S) : Samuel S.C. Yen, et. al.

It is certified that error appears in the above-identified patent and that said Letters Patent is hereby corrected as shown below:

In Column 14, line 34, please insert the word --a-- between the words "of" and "glucocorticoid".

Signed and Sealed this

Twenty-seventh Day of February, 2001

Attest:

NICHOLAS P. GODICI

Attesting Officer

Acting Director of the United States Patent and Trademark Office